United States Patent [19]
Canterna

[11] Patent Number: 5,156,168
[45] Date of Patent: Oct. 20, 1992

[54] SUPPORT FOR ARTHROSCOPY

[76] Inventor: A. C. Canterna, 380 W. Chestnut St., Washington, Pa. 15301

[21] Appl. No.: 664,334

[22] Filed: Mar. 4, 1991

[51] Int. Cl.⁵ .............................................. A61F 5/37
[52] U.S. Cl. ...................................... 128/879; 602/5; 602/21
[58] Field of Search ................ 128/77, 87 a, 878, 879, 128/880; 2/16; 602/5, 9, 12, 21, 22, 32, 36, 62

[56] References Cited

U.S. PATENT DOCUMENTS

| | | | |
|---|---|---|---|
| 2,511,182 | 6/1950 | Spencer | 128/84 |
| 2,783,758 | 3/1957 | Trott | 128/84 |
| 2,783,759 | 3/1957 | Hill | 128/133 |
| 3,049,717 | 8/1962 | Meyer | 2/16 |
| 3,176,683 | 4/1965 | Posey | 128/25 |
| 3,408,657 | 11/1968 | Gallagher | 2/159 |
| 3,769,970 | 11/1973 | Swanson | 128/77 |
| 3,774,242 | 11/1973 | Owen | 2/158 |
| 3,815,587 | 6/1974 | Guerrant | 128/77 |
| 4,193,135 | 3/1980 | Rhee | 2/162 |
| 4,281,647 | 8/1981 | Antypas | 128/77 |
| 4,574,398 | 3/1986 | Endo et al. | 2/159 |
| 4,628,911 | 12/1986 | Bornstein | 128/77 |
| 4,628,925 | 12/1986 | Witzel | 128/133 |
| 4,765,320 | 8/1988 | Lindemann et al. | 128/87 A |
| 4,796,306 | 1/1989 | Mitchell | 2/160 |
| 4,949,711 | 8/1990 | Gyovai et al. | 128/77 X |

Primary Examiner—Robert A. Hafer
Assistant Examiner—Sam Rimell
Attorney, Agent, or Firm—Webb, Burden, Ziesenheim & Webb

[57] ABSTRACT

A glove-like support for maintaining and positioning an arm during arthroscopy, comprising: a hand portion including at least two spaced apart attachment devices for attaching the glove-like support to an external support, each attachment device positioned at substantially a distal end of the hand portion; a wrist portion associated with the hand portion, the wrist portion being of sufficient width so as to support the weight of the arm without disrupting the blood support to a hand connected to the arm; a locking device associated with the wrist portion to cause the wrist portion to be tightly associated with the wrist of the arm; and a load distributing device extending substantially from the attachment device into the wrist portion to evenly balance, distribute and transfer the forces necessary to position and maintain the arm during arthroscopy between the attachment device and the wrist portion when the glove-like support is attached to the external support. The glove-like support of the present invention may be either sterile and disposable or sterilizable and reusable. In another embodiment of the present invention, the glove-like support includes a second inner glove interposed between the hand and the glove-like support to provide additional sterilization within the operative field and padding for the patient's comfort. The second inner glove may be either sterile and disposable or sterilizable and reusable.

24 Claims, 1 Drawing Sheet

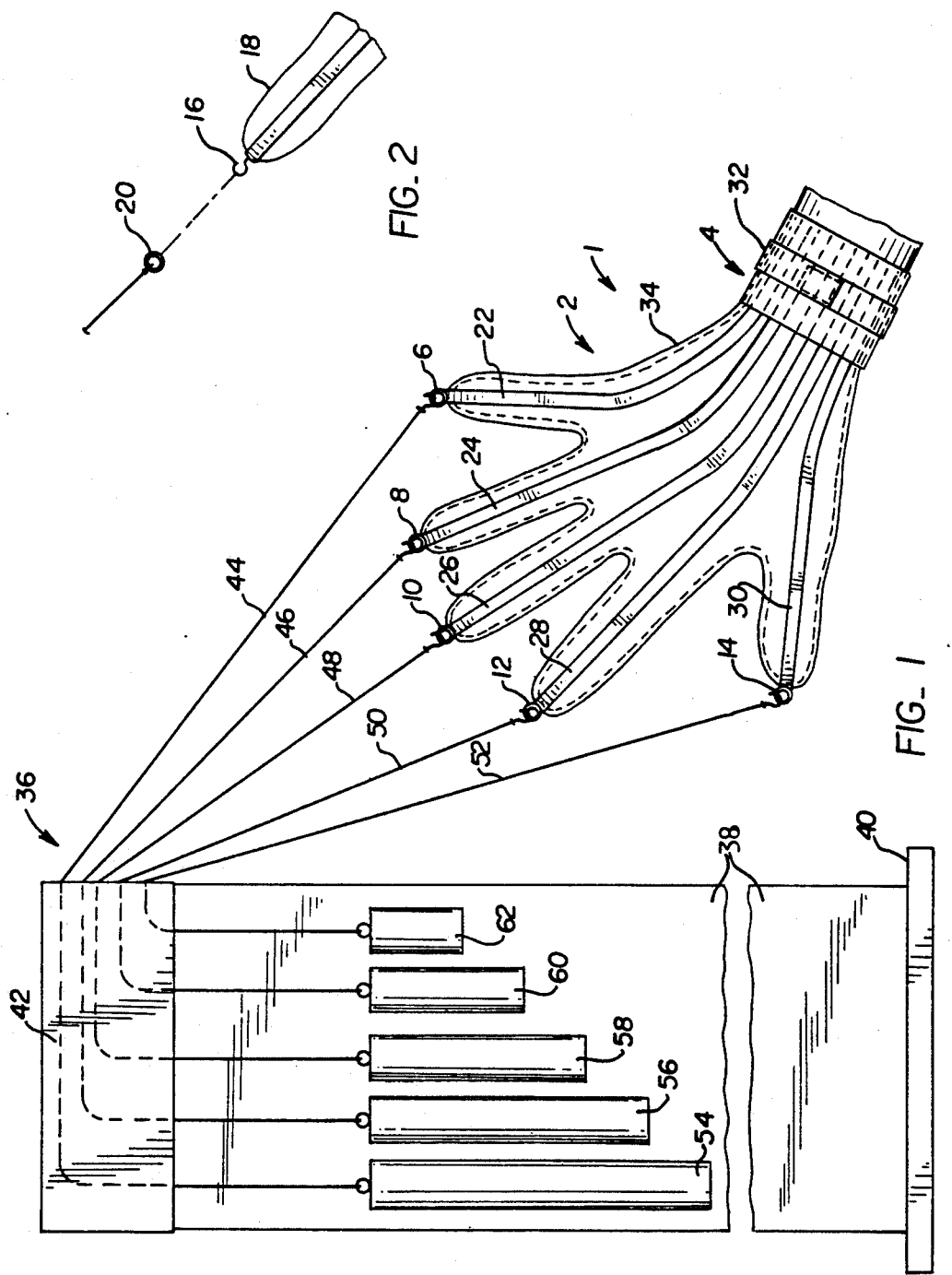

SUPPORT FOR ARTHROSCOPY

BACKGROUND OF THE INVENTION

1. Field of the Invention

The invention pertains in general to a device for maintaining and positioning limbs during surgical procedures and in particular to a device for maintaining and positioning an arm during arthroscopy.

2. Description of the Prior Art

Arthroscopy is a surgical procedure which permits a physician to examine the inside of joints such as the knee, shoulder and ankle. During the arthroscopic procedure, a small incision is made near the joint to be examined, and an arthroscope, which is a thin illuminated viewing scope with optical fibres on its tip, is inserted through the incision and is threaded into the joint by the physician. With the arthroscope, the physician can directly view the interior portion of the joint to assess the extent of damage and develop a plan of treatment.

During the threading process, the limb must often be rotated to permit the physician to thread the arthroscope to the joint to be examined. Furthermore, particularly with respect to shoulder arthroscopy, it is often necessary to position and maintain the patient's limb in a position above and away from the patient's body.

In the prior art, the patient's limb is maintained in a desired position during arthroscopy by affixing the limb to an external support such as a pole or stand, usually by tying the limb to the external support with supporting mechanisms such as tapes, ropes or straps. The process of attaching the tapes, ropes or straps to the patient's limb, and positioning the limb with the external support is a time consuming and cumbersome process resulting in a lengthy pre-operative set up period. The pre-operative set up period is lengthy in part because care must be taken to adequately support the limb without constricting its blood flow.

Furthermore, because an incision is made as part of the arthroscopic procedure, there is a need for sterilization in the field of operation. In the prior art, this meant that in addition to taping, roping or strapping the limb in the desired position, it was necessary to sterilize the field by either utilizing sterile support mechanisms and/or by wrapping the support mechanisms with sterile pads or towels. This also increases the pre-operative set up period.

In a typical prior art pre-operative set up procedure, the patient's limb is lifted to the approximate position. The limb is then sterilized with a sterilizing solution and is then draped with a sterile pad or towel. Next, the tape, rope or strap is affixed to the limb and the limb is in turn affixed to the external support.

In addition to the lengthy and cumbersome pre-operative set up procedure, the prior art also suffers from the limitation that often two or more of the surgical personnel are required to complete the set up procedure. A further limitation of the prior art procedure is that limbs wrapped with sterile pads or towels cannot be examined during the arthroscopic operation. Furthermore, it is also difficult to reposition or readjust the limb either during the operation or post-operatively.

Attempts have been made in the prior art to provide devices for supporting a patient's arm during shoulder arthroscopy. U.S. Pat. No. 4,628,911, issued Dec. 16, 1986 to Bornstein, discloses an arm suspension mitt for immobilizing and positioning a patient's arm for shoulder arthroscopy. While the above-cited reference represents an advance over the prior art, it does not completely fulfill the needs of the art because it does not allow for individual adjustment of the tension along each finger and thumb and further does not allow for the transfer of forces from the distal end of the fingers and thumb to the wrist in order to provide adequate support for the arm during arthroscopy without constricting the blood flow to the arm. Furthermore, the Bornstein reference requires inflation of an inflatable chamber and does not provide an effective means for easily repositioning the arm once the arm is suspended.

A need remains in the art for a support for limbs during arthroscopy which minimizes the pre-operative set up period, limits the number of surgical personnel necessary to perform the pre-operative set up, is fully adjustable during the operation and post-operatively, permits inspection of the limb while supported, permits quick and easy repositioning of the limb once the limb is suspended and which maintains a sterile operative field.

SUMMARY OF THE INVENTION

It is an object of the present invention to provide a support for surgical procedures in general and for arthroscopy in particular which fulfills the above-described needs in the art and overcomes the above-described limitations of the art by providing a glove-like support for maintaining and positioning an arm during arthroscopy, comprising: a hand portion including at least two spaced apart attachment devices for attaching the glove-like support to an external support, each attachment device positioned at substantially a distal end of the hand portion; a wrist portion associated with the hand portion, the wrist portion being of sufficient width so as to support the weight of the arm without disrupting the blood supply to a hand connected to the arm; a locking device associated with the wrist portion to cause the wrist portion to be tightly associated with the wrist of the arm; and a load distributing device extending substantially from the attachment device into the wrist portion to evenly balance, distribute and transfer the forces necessary to position and maintain the arm during arthroscopy between the attachment device and the wrist portion when the glove-like support is attached to the external support. The glove-like support of the present invention may be either sterile and disposable or sterilizable and reusable.

In another embodiment of the present invention, the glove-like support includes a second inner glove interposed between the hand and the glove-like support to provide additional sterilization within the operative field and padding for the patient's comfort. The second inner glove may be either sterile and disposable or sterilizable and reusable.

In a preferred embodiment, the locking device utilizes a hook and loop material. Also, in a preferred embodiment, the load distributing device includes stiffening ribs integrally associated with the hand portion of the glove-like support.

Also, in a preferred embodiment, the hand portion of the glove-like support of the present invention is a full glove, including four individual finger stalls and a thumb stall.

BRIEF DESCRIPTION OF THE DRAWING

FIG. 1 is a dorsal view of one embodiment of the glove-like support of the present invention showing an inner glove surrounded by an outer glove-like support, the outer glove-like support including eyelets which are associated with an external supporting stand; and FIG. 2 is a side view of an alternative embodiment of the present invention showing a hook associated with a representative finger/thumb stall.

DESCRIPTION OF THE PREFERRED EMBODIMENTS

Referring now to FIG. 1, there is shown a glove-like support for maintaining and positioning an arm during arthroscopy according to the present invention. Glove-like support 1 generally comprises hand portion 2 and wrist portion 4.

Hand portion 2 is shown in FIG. 1 by way of example as a full glove, including four individual finger stalls and a thumb stall. Hand portion 2 of glove-like support 1 further includes at least two spaced apart attachment devices 6, 8, 10, 12 and 14 for attaching glove-like support 1 to an external support. The attachment devices are positioned at substantially a distal end of hand portion 2, as shown in FIG. 1. These attachment devices are depicted in FIG. 1 as eyelets, however, any device will work which may be quickly and easily connected to an external support device. As shown in FIG. 2, the attachment device can be a metal or plastic hook 16 which is associated with thumb or finger stall 18, hook 16 being associated with eyelet 20, which is in turn associated with an external support device. Other devices suitable as attachment devices include hook and loop attachment devices such as Velcro®, available from Velcro USA, Inc. of Manchester, N.H.

In the preferred embodiment, hand portion 2 is a full glove including four individual finger stalls and a thumb stall, with each stall including an attachment device as shown in FIG. 1. In another embodiment of the present invention, hand portion 2 may comprise less than a full glove so long as there are at least two spaced apart attachment devices associated with the distal end of hand portion 2. Glove-like support 1, as shown and described in FIG. 1, may be made of a sterile and disposable material or, alternatively, it may be made of a sterilizable and reusable material such as nylon or Goretex®, available from W. L. Gore & Associates, Inc. of Newark, Del., both of which are easily gas sterilizable.

While the present invention requires at least two attachment devices 6, 8, 10, 12 and 14, the following discussion will assume that all attachment devices 6, 8, 10, 12 and 14 are utilized. Attachment devices 6, 8, 10, 12 and 14 are associated with wrist portion 4 through load distribution devices 22, 24, 26, 28 and 30, respectively. Load distribution devices 22, 24, 26, 28 and 30 are associated at a first end with attachment devices 6, 8, 10, 12 and 14, respectively, and are associated at a second end with wrist portion 4.

In a preferred embodiment of the present invention, load distribution devices 22, 24, 26, 28 and 30 extend into and are attached to wrist portion 4 substantially throughout the axial extent of wrist portion 4. This embodiment is preferred because the forces associated with supporting the patient's arm are distributed throughout the axial extent of wrist portion 4 and are not concentrated at an isolated attachment point(s) on wrist portion 4, providing for better overall support of the patient's arm. In one embodiment, load distribution devices 22, 24, 26, 28 and 30 extend into wrist portion 4 at least ½ to 1 inch. The attachment devices, load distribution devices and wrist portion 4 cooperatively function to evenly balance and distribute the forces necessary to position and maintain an arm in a desired orientation during arthroscopy when glove-like support 1 is attached to an external support device.

In one embodiment of the present invention, the distribution devices are stiffening ribs made of thickened ribs of the same base material as hand portion 2, such as reinforced nylon or Goretex®, integrally associated with hand portion 2. In another embodiment of the present invention, load distributing devices are metal or plastic wire or rod materials.

Wrist portion 4 is made of a flexible material such that it permits movement of the hand relative to the arm, i.e., wrist portion 4 bends with the natural wrist movements. Wrist portion 4 includes locking device 32 which is used to securely fasten wrist portion 4 to the patient's wrist. Any locking device which is known in the prior art and functions to secure wrist portion 4 to the patient's wrist may be utilized as part of the present invention. In a preferred embodiment, locking device 32 includes a cinching strap with Velcro® fastening means. In an alternative embodiment, locking device 32 is an elastic material. In another embodiment, locking device 32 is a belt and buckle or nylon web and hasp design. Wrist portion 4, as shown and described in FIG. 1, may be made of a sterile and disposable material or, alternatively, it may be made of a sterilizable and reusable material such as nylon or Goretex®, both of which are easily gas sterilizable.

Also shown in phantom in FIG. 1, is a second inner glove 34 which is optional to the present invention and which is shaped to generally conform to the human hand. Second inner glove 34 is interposed between glove-like support 1 and the patient's hand. Second inner glove 34 may be comprised of either a sterile and disposable material or a sterilizable and reusable material such as nylon or Goretex®. When utilized as part of the present invention, second inner glove 34 is placed over the patient's hand after the patient's hand has been sterilized, whereupon glove-like support is simply, easily and quickly placed over second inner glove 34, greatly reducing the set up time associated with this procedure.

Also shown in FIG. 1 is external support device 36. External support device 36 does not form a part of the present invention, but is shown to provide a full description of how the present invention is to be utilized. While external support device 36 could take any configuration known in the art which is suitable for supporting a limb, external support device 36 is shown in FIG. 1 as including pole 38 which is supported by base 40. External support device 36 further includes retaining device 42, opposite base 40, which is capable of maintaining supports 44, 46, 48, 50 and 52. In one embodiment of the present invention, these supports are associated at a first end with weights 54, 56, 58, 60 and 62, respectively, and are associated at a second end with glove-like support 1 with attachment devices 6, 8, 10, 12 and 14.

In this way, weights 54, 56, 58, 60 and 62 can be selectively modified to produce the desired tension on each of the four finger stalls and the thumb stall, which tension is then distributed evenly along distribution devices 22, 24, 26, 28 and 30 to wrist portion 4. In a preferred embodiment, retaining device 42 also includes a means to rotate supports 44, 46, 48, 50 and 52, whereby glove-like support 1, and in turn the patient's hand and arm, are rotated to any desired position by the physician. Similarly, in a preferred embodiment, the height of pole 38 is adjustable to permit vertical movement of a patient's hand and arm when supported by glove-like support 1 and external support device 36.

Having described the present invention, it is to be understood that it is not limited to this precise device and that changes may be made therein without departing from the scope of the invention which is defined in the appended claims.

I claim:

1. A glove-like support for maintaining and positioning an arm during arthroscopy, comprising:

a hand portion including finger portions and at least two spaced apart attachment means for attaching said glove-like support to an external support, each attachment means positioned at substantially a distal end of said hand portion;

a wrist portion associated with said hand portion, said wrist portion being of sufficient width so as to support the weight of said arm without disrupting the blood supply to a hand connected to said arm;

a locking means associated with said wrist portion to cause said wrist portion to be tightly associated with a wrist of said arm; and a load distributing means comprising a plurality of individual stiffening members extending substantially from said attachment means into said wrist portion to balance, distribute and transfer from said attachment means to said wrist portion, the forces necessary to support position, and maintain said arm in a desired orientation during arthroscopy when said glove-like support is attached to said external support.

2. The glove-like support of claim 1 wherein said hand portion is a full glove, including four individual finger stalls and a thumb stall.

3. The glove-like support of claim 2 wherein each of said stalls includes an attaching means.

4. The glove-like support of claim 1 wherein said glove-like support further includes a second inner glove shaped to generally conform to the human hand, said second inner glove being interposed between said glove-like support and said hand.

5. The glove-like support of claim 1 wherein said load distributing means extends into and is attached to said wrist portion substantially throughout the axial extent of said wrist portion.

6. The glove-like support of claim 1 wherein said load distributing means includes stiffening ribs integrally associated with said hand portion.

7. The glove-like support of claim 1 wherein said load distributing means includes one or more metal wires.

8. The glove-like support of claim 1 wherein said load distributing means includes a plastic or polymeric wire or rod material.

9. The glove-like support of claim 1 wherein said attaching means includes an eyelet.

10. The glove-like support of claim 1 wherein said attaching means includes a hook.

11. The glove-like support of claim 9 wherein said hook is made of metal.

12. The glove-like support of claim 9 wherein said hook is made of plastic or polymeric materials.

13. The glove-like support of claim 1 wherein said attaching means utilizes a hook and loop retaining means.

14. The glove-like support of claim 1 wherein said locking means includes a hook and loop fastening means.

15. The glove-like support of claim 1 wherein said locking means includes an elastic material.

16. The glove-like support of claim 1 wherein said locking means includes a strap and buckle.

17. The glove-like support of claim 4 wherein said second inner glove is surgically sterile and disposable.

18. The glove-like support of claim 4 wherein said second inner glove is surgically sterilizable and reusable.

19. The glove-like support of claim 1 wherein said glove-like support is surgically sterile and disposable.

20. The glove-like support of claim 1 wherein said glove-like support is surgically sterilizable and reusable.

21. The glove-like support of claim 6 wherein said stiffening ribs are made of thickened ribs of the same material as said hand portion.

22. The glove-like support of claim 3 wherein the forces transferred from said attachment means to said wrist portion by said load distributing means are transferred along individual lines.

23. The glove-like support of claim 22 wherein the force being transferred down each individual line may be independently varied.

24. The glove-like support of claim 3 wherein said four individual finger stalls and said thumb stall may be independently manipulated.

* * * * *